United States Patent [19]

Callne

[11] Patent Number: 5,221,203
[45] Date of Patent: Jun. 22, 1993

[54] CAST DENTAL MODEL ARTICULATOR

[76] Inventor: Lars E. Callne, 110 Los Patios, Los Gatos, Calif. 95030

[21] Appl. No.: 863,196

[22] Filed: Apr. 3, 1992

[51] Int. Cl.⁵ ............................................. A61C 11/00
[52] U.S. Cl. ....................................... 433/58; 433/57; 433/60
[58] Field of Search ....................... 433/54, 57, 58, 60, 433/61, 64, 65

[56] References Cited

U.S. PATENT DOCUMENTS

| | | | |
|---|---|---|---|
| 2,239,835 | 11/1937 | Zimmerman | 433/61 |
| 2,797,483 | 7/1957 | Lisowski | 433/57 |
| 2,865,102 | 12/1958 | Zelnigher | 433/58 |
| 3,808,689 | 5/1974 | Spinella | 433/60 |
| 4,365,955 | 12/1982 | Tradowsky | 433/57 |
| 4,968,256 | 11/1990 | Lang et al. | 434/263 |
| 5,076,786 | 12/1991 | Callne | 433/60 |

Primary Examiner—Gene Mancene
Assistant Examiner—Cindy A. Cherichetti
Attorney, Agent, or Firm—Thomas E. Schatzel

[57] ABSTRACT

The present invention comprises an articulator for registering an upper dental cast to a lower dental cast. The articulator includes an upper member subassembly with left and right sides and a lower member subassembly with left and right sides each composed of plastic material. The articulator further has at least one hinge member engaging one of the members allowing one of said members to pivot relative to the other member and a coupling means flexibly connecting the upper member subassembly to the lower member subassembly. The articulator further includes disconnectable connection means joined to one of the members for disengaging the upper member subassembly and the lower member subassembly whereby the upper and the lower member subassemblies may be separated, and a clipping means for removably securing the upper member subassembly to the upper dental cast and the lower member subassembly to the lower dental cast such that said upper and lower dental casts can be properly and flexibly aligned.

10 Claims, 1 Drawing Sheet

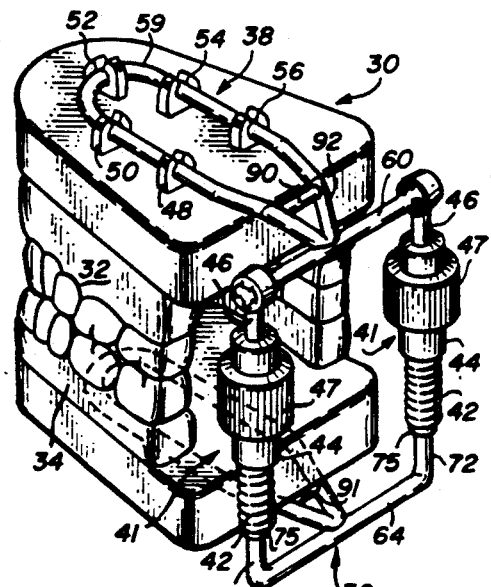
Fig. 1
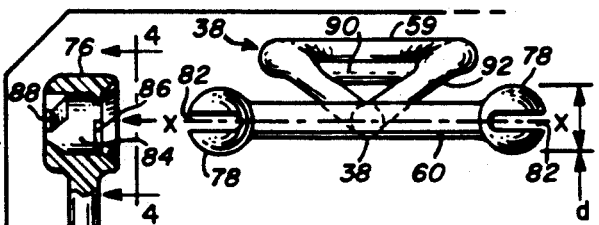
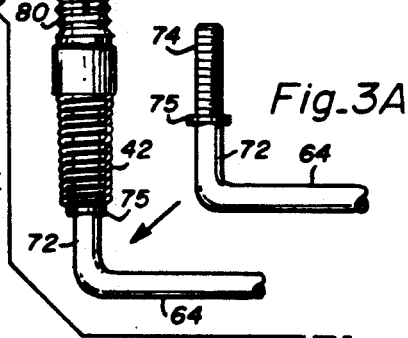
Fig. 3
Fig. 3A
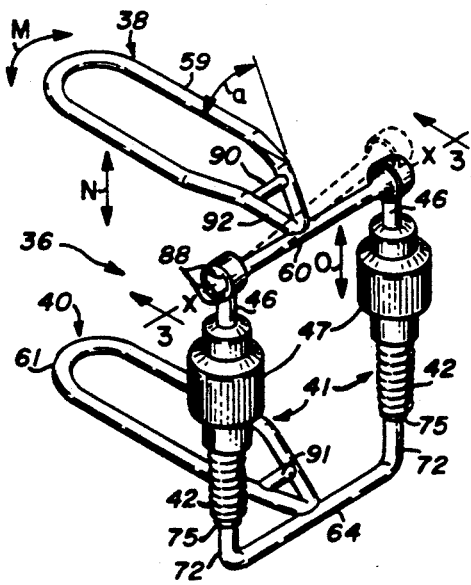
Fig. 2
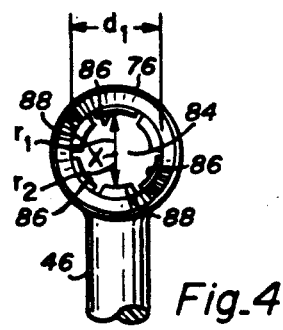
Fig. 4

CAST DENTAL MODEL ARTICULATOR

BACKGROUND OF THE INVENTION

1. Field of the Invention

This invention relates generally to a dental apparatus for assisting dentists and technicians working with cast dental models for constructing prosthetic denture elements outside the patient's mouth. More particularly, this invention relates to an improved articulator which provides for flexible adjustability, convenient use and mass-production.

2. Description of the Prior Art

It is important that articulators used for supporting impressions of human jaws with artificial teeth including a lower jaw model and an upper jaw model, be capable of simulating the full range of occlusal and masticatory registrations among the patient population. The lower jaw model and the upper jaw model are supported by the articulator to be positioned in a contiguous relationship to provide centric, lateral and protrusive movement relative to each other and to simulate a patient's bite. While there are a wide variety of shapes, sizes and arrangements of human jaws and teeth, configurations and occlusion patterns have a broad range among different patients. Nevertheless, the process of making a jaw impression and the fabrication of partial dentures, fixed bridges and crowns by using jaw models in a dental laboratory requires that precise registration and desired occlusal alignment be maintained. Therefore, in order to satisfy this full range registration requirement, it often requires use of articulators which are complex, difficult to operate and expensive.

An articulator which has a wide range of registration and is simple to use, has been disclosed by Callne in U.S. Pat. No. 5,076,786, entitled "Cast Dental Articulator System and Method", issued on Dec. 31, 1991 wherein an articulator comprising two U-shaped wire frames is disclosed. These two frames are joined by hinges and springs. The frames may be snapped onto plastic clips cemented to the dental casts whereby the dental casts may be easily removed and reattached to the articulator in a highly repeatable manner. A slip-joint also provides the flexibility for left and right height adjustment to fit a wide range of dental cast models. The slip-joint further allows the upper wire frame to be completely separated from the lower wire frame.

While the articulator as disclosed in the aforementioned Callne Patent has a wide range of registration and is simple to use, it is desirable to provide an articulator structure with greater adjustment flexibility which is also renderable to being manufactured of light weight materials.

SUMMARY OF THE PRESENT INVENTION

It is therefore an object of the present invention to provide an articulator that has flexible adjustments.

It is another object of the present invention to provide an articulator that may be manufactured from lightweight materials.

It is another object of the present invention to provide an articulator wherein the frames, hinges and lock dowels may be composed of plastic materials and therefore easily mass-produced to achieve lower production cost.

It is another object of the present invention to provide an articulator with flexible hinges and slip-joint structure whereby the upper and lower frames can be easily assembled to engage the hinges.

Briefly, in a preferred embodiment, the present invention comprises an articulator for registering an upper dental cast to a lower dental cast. The articulator comprises an upper frame member subassembly for engaging an upper dental cast and having left and right sides, and a lower frame member subassembly for engaging a lower dental cast and having left and right sides with each frame member subassembly composed of plastic material. The articulator further has two vertical arms interconnected by a hinge also engaged to the upper member subassembly. Each arm has at least one hinge support engaging each side of one of the frame member subassemblies and thereby allowing at least one of the frame member subassemblies to be pivoted relative to the other frame member subassembly. Also, a coupling means is engaged to the vertical arms to connect the upper frame member subassembly to the lower frame member subassembly and provide a disconnectable means for engaging and disengaging the upper frame member subassembly and the lower frame member subassembly whereby the upper and the lower frame member subassemblies may be separated. The upper frame member subassembly is engaged at the midpoint of the hinge. A clipping means provides for removably securing the upper frame member subassembly to an upper dental cast and the lower frame member subassembly to a lower dental cast.

An advantage of the present invention is that it provides an articulator that provides for flexible adjustments.

Another advantage of the present invention is that it provides for an articulator which may be manufactured from light weight materials.

Another advantage of the present invention is that it provides an articulator wherein the frames, hinges and lock dowels may be composed of plastic materials and therefore easily mass-produced to achieve lower production cost.

Another advantage of the present invention is that it provides great flexibility to conform to non-parallel dental cast models.

Another advantage of the present invention is that it provides an articulator with flexible hinges and slip-joint structure whereby the upper and lower frames can be easily assembled to engage the hinges.

These and other objects and advantages of the present invention will no doubt become obvious to those of ordinary skill in the art after having read the following detailed description of the preferred embodiment which is illustrated in the various drawing figures.

BRIEF DESCRIPTION OF THE DRAWINGS

FIG. 1 is a perspective view of an articulator of the present invention attached to two dental casts by clips;

FIG. 2 is an elevational view of the articulator of FIG. 1 shown without the dental casts and clips;

FIG. 3 is a partial elevational view of the articulator of FIG. 2 showing a dowel-hinge of the upper frame member subassembly and a vertical arm subassembly extending to the lower frame member subassembly;

FIG. 3A is a partial elevational view of the end of the cross-bar of the lower frame member subassembly of FIG. 3 separate from the compression nut and the sleeve; and FIG. 4 is an end view of the socket of the dowel-hinge of the articulator of FIGS. 1-3 taken along the line 4—4 of FIG. 3.

DETAILED DESCRIPTION OF THE PREFERRED EMBODIMENT

FIG. 1 shows an exemplary articulator system, referred to by the general reference numeral 30 wherein an upper dental cast 32 and a lower dental cast 34 are supported by an articulator 36. As illustrated in FIGS. 1-3, the articulator 36 comprises an upper frame member subassembly 38, a lower frame member subassembly 40, and a pair of vertical subassemblies 41. Each subassembly 41 includes a spring coil 42, a threaded, hollow, slip joint frame 44, a dowel 46 and a threaded nut 47. A plurality of clips 48, 50, 52, 54 and 56 secure the upper dental cast 32 to the upper frame member subassembly 38. Though not shown, the lower dental cast 34 is secured to the lower frame member subassembly in a similar manner.

The upper frame member subassembly 38 comprises an upper mounting frame 59 forming a closed loop extending forward from the middle portion of a hinge bar 60. The lower frame member subassembly 40 comprises a lower mounting frame 61 forming a closed loop extending forward from the middle portion of a cross bar 64.

The upper frame member subassembly 38 and the lower frame member subassembly 40 are interconnected through the vertical subassemblies 41. The cross bar 64 is U-shaped with both ends projecting upwardly to form two joint bars 72 each with a threaded end 74 and a collar stop 75 (See FIG. 3A) which can be securely threaded to the bottom end of the coil springs 42. The other end of the springs 42 are each connected to the threaded slip joints 44 which in turn receives one end of the dowels 46 and the nut 47. Assembled, the nut 47 locks one end of each of the dowels 46 securely within the top of the portion of the slip joints 44. The other end of each of the dowels 46 has a bowl-shaped socket hinge receptacle 76. Each end of the hinge bar 60 comprises a spherical ball-shaped hinge means 78 with each of the hinge means 78 engaging one of the hinge receptacles 76 to form a ball-and-socket relationship such that the hinge bar 60 may be rotated and revolved with the hinge receptacle. Thus the upper frame member subassembly 38 can pivotally move relative to the dowels 46 as shown by the arrows M—M in FIG. 2 and be pivoted about the axis X of the bar 60 as shown by the arrows N—N.

The upper frame member subassembly 38, the lower frame member subassembly 40 and the dowels 46 may all be composed of plastic materials. Referring to FIGS. 2 and 3, as illustrated, the elevation of each of the dowels 46 may be independently adjusted depending on its position within its associated slip joint 44. Likewise each end of the hinge bar 60 may be at an independent elevation as a result of the ball-and-socket arrangement of the socket-shaped hinge receptacle 76 and ball-shaped hinge means 78. The articulator 36 provides for convenient adjustments in X, Y, and Z ordinate planes such that accurate simulations of the occlusal registration can be accomplished. Additionally, due to the flexibility of its structure, the upper frame member subassembly 38 with its hinge means 78 can be removed from and re-installed in the hinge receptacles 76 merely by hand manipulations and without requiring prior removal of the dowels 46 from the slip joints 44. Thus, the operational procedures in assembling and disassembling the articulator 36 to support the cast dental models are thereby simplified because the assembly and disassembly can be performed either with or without the casts 32 and 34 in place and without any tools.

FIG. 3 further illustrates the details of how the upper frame member subassembly 38 is connected to the lower member subassembly 40 through the vertical subassemblies 41. The slip joints 44 each include a slot 79 to form a a split compression sleeve with threads 80 to receive the compression nut 47. The slip joints 44 are hollow with a cross-sectional diameter slightly less than the outer diameter of dowels 46 such that the dowels can be slid within the joints 44. Thus the nut 47, when threaded down on the threads 80 causes the compression sleeve to lock the associated dowel 46 into the selected elevational position. The slip joints 44 allow the dowels 46 to be individually adjusted as illustrated by the line O—O and then locked into a selected position thus allowing both the height and the lift tilt of the hinge bar 60 to be adjusted.

FIG. 3 further illustrates the hinge assembly. The hinge means 78 about each end of the hinge bar 60 is a spherical ball with an internal U-shaped slot 82. Thus slot 82 provides for some compression of the hinge means 78 and some flexibility when external pressures are applied. As illustrated in FIGS. 3 and 4 the socket receptacle 76 comprises a bowl-shaped cavity 84 having a diameter $d_1$ and including two sets of securing ridges, i.e. a set of three outer ridges 86 and a set of three inner ridges 88 disposed within and about the internal peripheral of the cavity 84. The cross-sectional diameter d of the ball of the hinge means 78 is slightly larger than twice the radius $r_1$ of the outer ridges 86 within receptacle 76, and significantly greater than twice the radius $r_2$ of the inner ridges 88 such that the hinge means may be cupped within the cavity 84 intermediate the ridges 86 and 88. The hinge means 78 can be positioned in the cavity 84 by asserting a hand pressure along the axis x to insert the hinge means 78 into the hinge cavity 84. As the hand pressure is applied, the ball-shaped hinge means 78 is placed against the outer ridges 86 and the responsive pressure from the outer ridges 86 causes the ball 78 to compress thereby closing the slot 82 and allowing the ball 78 to pass between the outer ridges 86 and be secured in the cavity 84. The ridges 88 simultaneously limit the degree of movement along the X-axis. The cross-sectional diameter of the cavity space 84 as surrounded by the inner ridges 88 is significantly smaller than the cross-sectional diameter of the hinge means 76 thus preventing the hinge means 78 from being pushed out of the cavity space 84 along the X-axis. Conversely, the hinge means 78 can also be removed from the receptacle 76 by applying a hand removing force pulling the hinge means 78 away from the hinge cavity 84 along the X-axis.

In one example of the preferred embodiment, the diameter $d_1$ of the cavity 84 is approximately 0.245 inches, radius $r_1$ is approximately 0.1125 inches and the radius $r_2$ is approximately 0.0925 inches. The hinge means 78 has a diameter d of approximately 0.240 inches and the gap of 82 has a width of approximately 0.062 inches. Because the diameter of the ball of the hinge means 78 is slightly smaller than that of the cavity 84, the hinge means 78 and the upper member subassembly 38 has a small clearance, i.e. 0.05 inches, thereby allowing for rotational and revolving motion. This allows for significant diverse elevational positions of the dowels 46 relative to one another and without impairing the rotational movement of the hinge bar 60. Thus, non-parallel dental casts 32 and 34 can be readily accommodated.

Thus, the articulator 36 can flexibly simulate the full range of occlusal registrations as experienced with a wide range of patients. In the meantime, the hinge means 78 is secured along the X axis by the ridges 86 and 88 without significant lateral movement whereby a precise control of occlusal alignments can be maintained.

As illustrated by FIGS. 3 and 4, the outer ridges 86 and the inner ridges 88 are disposed on the internal peripheral of the hinge cavity 84 in a non-overlapping manner. The three ridges 86 are distributed on the peripheral in three angular spaces while the three ridges 88 are distributed in three complimentary angular spaces. This design simplifies the manufacturing process, thus reducing the unit cost of the articulator 36, and allows more degree of freedom for the hinge means 78 including ball-shaped hinge means 80 to rotate to different angular position in the hinge cavity 84. For example, the dowel 46 with the receptacle can be made with a single plastic mold. Likewise, the upper frame member subassembly 38 may be made with a single plastic mold as can the lower frame member subassembly 40.

Referring to the structures of the upper frame member subassembly 38 and the lower frame member subassembly 40, mounting frame 59 forms a closed loop projecting from the hinge bar 60 and the mounting frame 61 forms a closed loop projecting from the cross bar 64. Each is reinforced with a reenforcing bar 90 and 91, respectively, to strengthen the structure. The upper mounting frame 59 extends forward and elevated at an angle "a" relative to the hinge bar 60. The elevation results from interconnection of the V-shaped brace 92 formed by the bar 90 and extensions interconnecting the bar 60 and frame 59. The apex of the V-shaped brace 92 is positioned at the mid-point of the bar 60 such that the fulcrum arms between the apex and the hinge assemblies are equal and balanced. The brace 92 is at the angle "a" of approximately forty degrees from the horizontal plane of frame 59. The frame 59 then projects from the V-shaped brace 92 at a plane parallel to the X-axis of the bar 60. This angular structure of the upper mounting frame 59 established by the brace 92 provides for additional flexibility of the articulator 36 and the depth of dental casts 32 and 34 which can be accommodated. For example, the upper frame member subassembly 38 may be positioned between the vertical assemblies 41 with the frame 59 above the elevation of the x-axis, as shown in FIGS. 1-3, or below the elevation of the x-axis. When below the plane of the x-axis, the vertical spacing between the frames 59 and 61 is less than that when above the plane of the x-axis.

The length that the upper mounting frame 59 extends forward from the hinge bar 60 is approximately 2.55 inches which is substantially the same as the projection of the lower mounting frame 61 from the cross bar 64. The length of the hinge bar 60 is approximately 2.00 inches and that of the cross bar 64 is approximately 1.77 inches. All of the components except for the coil spring 42 are composed of a plastic material. The coil spring 42 slip joint 44 and nut 47 are composed of stainless steel.

Although the present invention has been described in terms of the presently preferred embodiment, it is to be understood that such disclosure is not to be interpreted as limiting. Various alterations and modifications will no doubt become apparent to those skilled in the art after reading the above disclosure. Accordingly, it is intended that the appended claims be interpreted as covering all alterations and modifications as fall within the true spirit and scope of the invention.

I claim:

1. An articulator for registering an upper dental cast to a lower dental cast comprising:
   an upper frame member subassembly and a lower frame member subassembly, the upper frame subassembly including an upper mounting frame in the shape of a closed loop structure;
   at least one hinge member engaged to one of the frame member subassemblies such that one of the frame subassemblies can be pivoted relative to the other frame member subassembly said upper mounting frame subassembly extending forwardly from the hinge member, the hinge member including left and right ends with each end forming a ball-shaped member with an internal U-shaped slot;
   coupling means flexibly connecting the upper frame member subassembly to the lower frame member subassembly, the coupling means further including at least two arms with each arm including a socket for receiving the hinge member about one end of the coupling means and one end of the hinge member with each of said ball-shaped members interengaged with one of said sockets to form a coupling assembly for pivotally securing the hinge member;
   disconnectable connection means intermediate the frame member subassemblies for disengaging the upper frame member subassembly from the lower frame member subassembly; and
   means for removably securing the upper frame member subassembly to an upper dental cast and the lower frame member subassembly to a lower dental cast such that the relative alignment between said upper and lower dental casts can be adjusted.

2. The articulator of claim 1 wherein:
   each of said sockets have an internal diameter slightly greater than the external diameter of said ball-shaped members whereby the sockets receive and securely engage the hinge member.

3. The articulator of claim 2 wherein:
   each of said sockets further include a plurality of outer ridges disposed at the outer peripheral of said socket wherein a cavity space is surrounded by said outer ridges having a diameter slightly smaller than said outer diameter of said ball-shaped member whereby said hinge member may be inserted into said cavity by applying a hand pressure forcing said ball-shaped member to pass said outer ridges.

4. The articulator of claim 3 wherein:
   each of said sockets further includes a plurality of inner ridges disposed at the inner peripheral of said socket and diametrically spaced at a distance substantially less than said external diameter of said ball-shaped members whereby said hinge member is securely engaged in said sockets.

5. The articulator of claim 4 wherein:
   the upper frame member subassembly further includes a re-enforcing bar within said closed loop and including two ends with each end attached to said frames whereby the upper frame member subassembly is strengthened.

6. The articulator of claim 5 wherein:

said upper frame member subassembly projects from the hinge member at an elevational angle relative to the axis of the hinge member.

7. The articulator of claim 1 wherein:

the lower frame member subassembly further comprises a lower mounting frame for clipping to clipping means, the lower frame member subassembly extending forwardly from a joint frame including left and right joint bars extending upwardly from the lower frame member subassembly; and said joint bars being engaged to the couping means.

8. The articulator of claim 7 wherein:

the lower mounting frame forms a closed loop with a reenforcing bar within said closed loop and including two ends with each end attached to said frame whereby the lower frame member subassembly is strengthened.

9. An articulator for registering an upper dental cast to a lower dental cast comprising:

an upper frame member subassembly with left and right sides and a lower frame member subassembly with left and right sides each composed of plastic material;

a coupling means flexibly connecting the upper frame member subassembly to the lower frame member subassembly;

the upper frame member subassembly further comprises an upper mounting frame being a substantially closed-loop structure extending forwardly and at an acute elevational angle relative to a hinge bar, said hinge bar including left and right ends with each end including a hinge means of a substantially ball-shaped hinge with an internal opening;

a pair of hinge socket members engaging said hinge bar and the upper member, each of the hinge socket members including a hinge cavity having a diameter slightly greater than the diameter of said ball-shaped hinge means whereby the hinge cavities receive and securely engage said hinge means, and each of said hinge cavities further including a plurality of outer ridges disposed at the outer peripheral of said cavity wherein a cavity space surrounded by said outer ridges is formed and having a diameter slightly smaller than the diameter of said ball-shaped hinge means whereby said hinge means may be inserted into said hinge cavity by applying a hand pressure forcing said ball-shaped hinge means to pass said outer ridges, each of said hinge cavities further including a plurality of inner ridges disposed at the inner peripheral of said cavity and diametrically spaced at a distance substantially less than the external diameter of said ball-shaped hinge means whereby said hinge means are securely engaged in said hinge cavities;

said upper frame member subassembly further includes a first re-enforcing bar within said closed loop and including two ends with each end attached to said frame whereby the upper frame member subassembly is strengthened;

the lower frame member subassembly further includes a lower mounting frame forming a closed loop extending forwardly from a joint frame including left and right joint bars extending upwardly from the lower frame member subassembly, said joint bars being engaged to the coupling means, said lower mounting frame forms a second closed loop, and a second re-enforcing bar within said second closed loop including two ends with each end attached to said lower mounting frame;

disconnectable connection means intermediate the frame member subassemblies for disengaging the upper frame member subassembly from the lower frame member subassembly; and clipping means engaging said left and right sides of the upper and lower frame subassemblies for removably securing the upper mounting frame to said upper dental cast and the lower mounting frame to said lower dental cast such that said upper and lower dental casts can be flexibly aligned.

10. an articulator for registering an upper dental cast to a lower dental cast comprising:

an upper frame member subassembly and a lower frame member subassembly, the upper frame subassembly including an upper mounting frame;

at least one hinge member engaged to one of the frame member subassemblies and including left and right ends with each end forming a ball-shaped member with an internal U-shaped slot such that said engaged frame subassembly extends forwardly from the hinge member and can be pivoted relative to the other frame member subassembly;

coupling means flexibly connecting the upper frame member subassembly to the lower frame member subassembly, the coupling means further including at least two arms with each arm including a socket for receiving the hinge member about one end of the coupling means and one end of the hinge member with each of said ball-shaped members interengaged with one of said sockets to form a coupling assembly for pivotally securing the hinge member;

disconnectable connection means intermediate the frame member subassemblies for disengaging the upper frame member subassembly from the lower frame member subassembly; and means for removably securing the upper frame member subassembly to an upper dental cast and the lower frame member subassembly to a lower dental cast such that the relative alignment between said upper and lower dental casts can be adjusted.

* * * * *